United States Patent [19]

Morris et al.

[11] Patent Number: 4,874,364
[45] Date of Patent: Oct. 17, 1989

[54] INSPECTION INSTRUMENT CHANNEL ASPIRATOR AND PRESSURE NEUTRALIZING DEVICE

[75] Inventors: David L. Morris, Melton-Mobray, England; Mihail Filip, Shelton, Conn.; Frank D. D'Amelio, Oxford, Conn.; Dominick G. Esposito, Danbury, Conn.; Robert H. Quint, Jamaica, N.Y.

[73] Assignee: Circon Corporation, Santa Barbara, Calif.

[21] Appl. No.: 171,569

[22] Filed: Mar. 22, 1988

[51] Int. Cl.[4] .............................................. A61M 1/00
[52] U.S. Cl. ....................................... 604/35; 604/119; 128/4; 251/149.1
[58] Field of Search .................. 604/35, 119, 118, 171, 604/172, 110, 45, 122, 164, 167, 169; 128/4-6; 251/149.1

[56] References Cited

U.S. PATENT DOCUMENTS

| | | | |
|---|---|---|---|
| 3,958,566 | 5/1976 | Furihata et al. | 604/119 |
| 4,198,958 | 4/1980 | Utsugi | 604/119 |
| 4,240,411 | 12/1980 | Hosono | 604/167 |
| 4,270,525 | 6/1981 | Furihata | 604/119 |
| 4,311,137 | 1/1982 | Gerard | 604/167 |
| 4,561,428 | 12/1985 | Konomura | 604/119 |
| 4,562,830 | 1/1986 | Yabe | 604/119 |
| 4,661,110 | 4/1987 | Fortier et al. | 604/284 |
| 4,805,611 | 2/1989 | Hodgkins | 604/171 |
| 4,809,679 | 3/1989 | Shimonaka et al. | 604/167 |

FOREIGN PATENT DOCUMENTS 2365157 4/1976 France .............................. 604/119
35387 7/1963 German Democratic Rep. .

Primary Examiner—C. Fred Rosenbaum
Assistant Examiner—Kathleen A. Daley
Attorney, Agent, or Firm—Perman & Green

[57] ABSTRACT

A gas pressure neutralizing device for use with a working channel of an inspection instrument. The device comprises means for providing a first gas pressure buffer, a second gas pressure buffer, a chamber formed therebetween and means for reducing the pressure in the chamber whereby gases are substantially prevented from exiting the instrument through a working inlet of the device at an elevated pressure or high velocity.

22 Claims, 2 Drawing Sheets

INSPECTION INSTRUMENT CHANNEL ASPIRATOR AND PRESSURE NEUTRALIZING DEVICE

BACKGROUND OF THE INVENTION

1. Field of the Invention

The present invention relates to instruments for accessing target areas and, in particular, to an inspection instrument having a pressure neutralizing device for use with a working channel of the instrument which may be in the form of an Aspirator.

2. Prior Art

Elongated tubular inspection devices, particularly such devices incorporating fiber-optics, are often used to inspect sites which would not normally be visible to the human eye. One application of such tubular inspection devices is in the practice of medicine. For instance, a common form of such device, known as a colonoscope, is used for the inspection of the human colon area.

The colonoscope is conventionally used for a variety of functions such as observation of areas and presenting a working tool at the area for such things as polyp snaring, taking biopsies, treating bleeders with Bicap probes, etc. The colonoscope examination can involve the physician's placing the instrument in the body through the rectum and then into the colon. The inspection instrument generally has a control head forming a proximal end and a tubular shaft, the end of which forming a distal end. The physician observes target areas through an eyepiece in the control head. Generally, the colonoscope is provided with a bundle or bundles of optical fibers which bring light to its objective end, the end which is placed adjacent the area to be examined, and a bundle or bundles of image transmitting fibers through which an image of the examined area is transmitted back to the eyepiece. The colonoscope generally further incorporate a working channel which provides a conduit for providing washing fluid to the site under examination as well as for the introduction of accessory devices to the site such as a biopsy forceps.

The control head of a colonoscope is generally capable of serving many purposes including housing the optical eyepiece assembly, providing an entry for a light carrier from a light source, housing a deflection control system for moving and controlling the distal end and providing an entry for tools and fluids to enter into the control head and be transported to the objective end by means of the working channel.

In one method of performing a visual examination of the colon by use of a colonoscope, pressurized air is provided in the colon for expansion thereof. However, the use of pressurized gases in this fashion causes problems with the use of the colonoscope. In particular, the pressurized gases have a tendency to exit the colon through the working channel of the colonoscope in addition to spitting extraneous material such as fluids and the like from the end of the working channel. This is especially a problem when the operator removes the working instrument from the working channel.

It is therefore an objective of the present invention to provide a device for preventing pressurized gases and extraneous material from spitting out of the working channel of an inspection instrument.

It is a further objective of the present invention to provide an aspirator for the working channel of an inspection instrument to suck off extraneous material such as fluids and the like.

It is a further objective of the present invention to provide a device for cleaning a working instrument as it is exited from a working channel of a inspection instrument.

It is a further objective of the present invention to provide a gas pressure neutralizing device for use with a working channel of an inspection instrument which is detachably mounted thereto.

SUMMARY OF THE INVENTION

The foregoing problems are overcome and other advantages are provided by a gas pressure neutralizing device for use with a working channel of an inspection instrument.

In accordance with one embodiment of the invention, the device comprises means for providing a first gas pressure buffer between the working channel of the instrument and a chamber means of the device. The gas pressure buffer means is provided with a first means for passage of a working instrument therethrough. The device also comprises means for providing a second gas pressure buffer between the chamber means and a working inlet of the device. The second pressure buffer means also has a second means for passage of the working instrument therethrough. Means are provided for reducing the pressure in said chamber means whereby gases passing through the working channel are substantially prevented from exiting through the working inlet at an elevated pressure.

In accordance with an alternate embodiment of the invention, an aspirator for use with a working channel of an inspection instrument comprises first seal means having means for passage of a working instrument therethrough. The first seal means is positionable proximate the working channel. A second seal means is provided having means for passage of the working instrument therethrough. Chamber means is provided between the first seal means and the second seal means. Means for reducing the pressure of gases in the chamber means is provided whereby gases passing through the working channel are substantially prevented from exiting through a working inlet of the aspirator at an elevated pressure.

In accordance with one method of the invention, the method comprises the steps of providing a first seal means proximate the working channel of the instrument, the first seal means having means for passage of a working instrument therethrough; providing a second seal means having means for passage of the working instrument therethrough, said first and second seal means forming a chamber means therebetween; and exiting at least a portion of the gases in the chamber means through an exit port whereby gases passing through the working channel are substantially prevented from exiting a working inlet at an elevated pressure or velocity.

BRIEF DESCRIPTION OF THE DRAWINGS

The foregoing aspects and other features of the invention are explained in the following description, taken in connection with the accompanying drawings wherein.

DETAILED DESCRIPTION OF THE INVENTION

Figure 1:
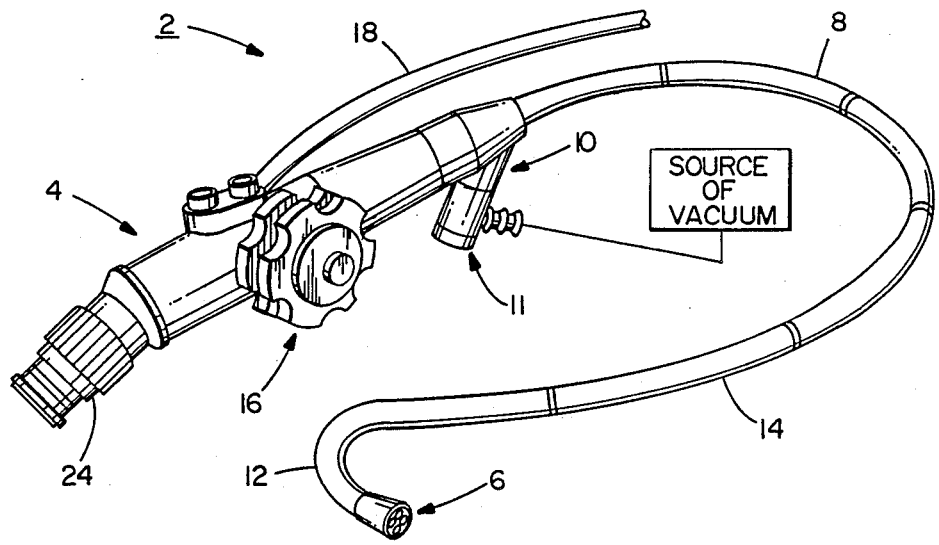
FIG. 1 is a perpsective view of an inspection instrument having a gas pressure neutralizing device comprising features of the invention.

Referring to FIG. 1 there is shown one embodiment of a flexible inspection instrument 2, incorporating features of the invention. The inspection instrument 2, in this embodiment, is a flexible colonoscope which is generally used for internal examinations and operations on the human body and, more particularly, for use in the colon area of the body. However, the present invention can be used with any type of inspection instrument including gastroscopes. The colonoscope 2 has a proximal control head 4, a distal objective head 6 and a tubular flexible shaft 8 interconnecting the control head 4 to the objective head 6.

The tubular flexible shaft 8 is generally capable of conveying the objective head 6 to the site to be examined. In addition, the shaft 8 also defines a tubular passage 26 for elongate components to extend through the shaft from an entry port section 10 on the control head 4 to the objective head 6. The tubular flexible shaft 8, in this embodiment, includes a relatively short distal deflector section 12 connected to the objective head 6 and an extended proximal flexible section 14 between the distal deflector section 12 and the control head 4. The distal deflector section 12 is generally adjustable in a controlled manner at the control head 4 via a deflection control 16 for manipulating the objective head 6 over the entire site, such as a body cavity, being examined and to this end has a high degree of flexibility. The flexible shaft section 14, however, can be less flexible, being required to flex only sufficiently to follow the contours of the canal or tract leading to the target area.

For inspecting the site to be examined, in this embodiment, the colonoscope has an optical system including an external light carrier or bundle of light transmitting fibers 18 for carrying light from a lamp box or light source for illuminating the inspection site. In the embodiments shown, the carrier 18 has a control head connector which connects a light post assembly on the control head 4. A first light carrier (not shown) is located in the instrument 2 and receives light from the external light carrier 18 at the light post assembly. The first internal light carrier travels through the control head 4 and through the flexible shaft 8 to the objective head 6. The carrier then provides light to the inspection site. An image received from the illuminated site is conveyed back to an eye piece assembly 24 by a second internal light carrier or image bundle (not shown) and suitable optical system (not shown). Using the eye piece assembly 24 the physician or clinician can view the operative field and follow the movement of the distal end of the flexible shaft relative to the operative field. The excessory passage or working channel 26 extends from the control head 4 through the flexible shaft 8 to terminate in an open end in the objective head 6 and is excessible through the entry port section 10 mounted on the control head 4. In the embodiment shown, the entry port section 10 is fixedly mounted to the control head. However, any suitable means can be provided for manufacturing the control head 4 with any suitable type entry port.

Figure 2:
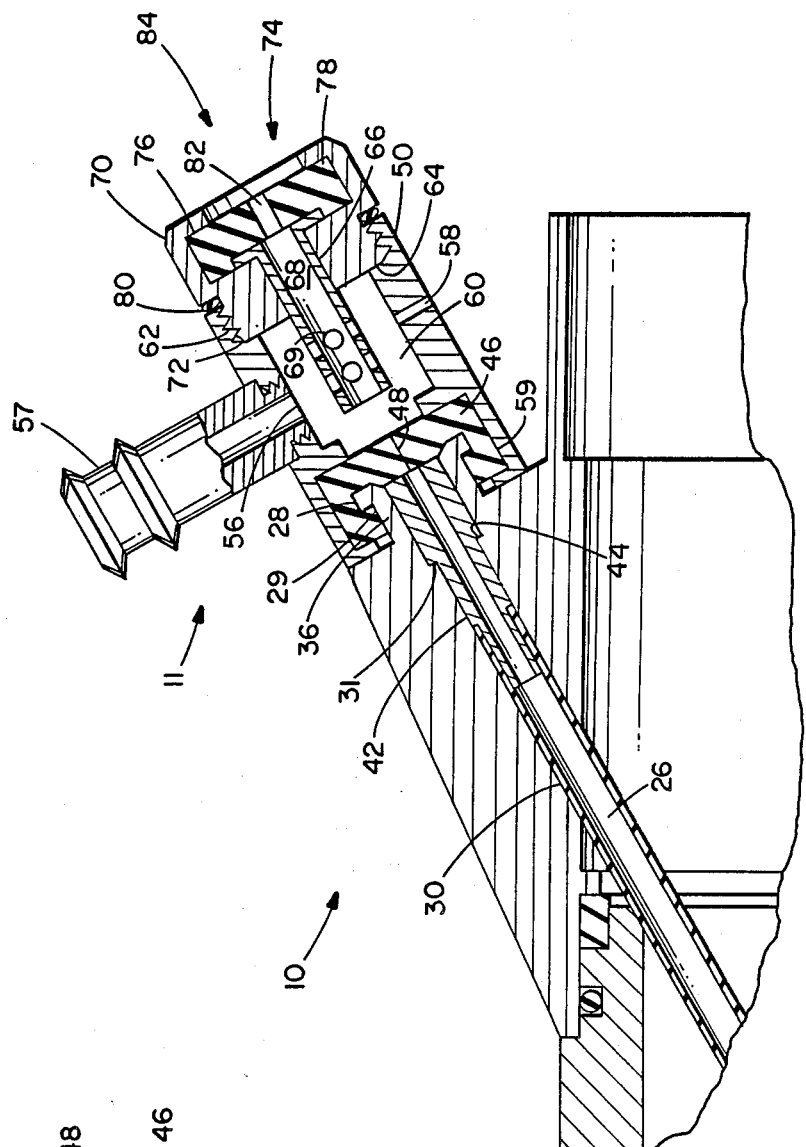
FIG. 2 is an enlarged cross-sectional view of the device shown in FIG. 1 attached to the control head of the inspection instrument.

Referring now to FIG. 2, a cross-sectional view of the working instrument entry port section 10 is shown. The entry port section 10 has an entry passage or accessory aperture 30. Located in the passage 30 is a first ledge 31. At a top section there is an entry port 36 having an enlarged rim 28 and neck 29. Located within the entry block aperture 30, in this embodiment, is a working channel end fitting 42. The end fitting 42 has a proximal end of the working channel 26 attached thereto. The fitting 42 is generally inserted into the entry aperture 30 until a ledge 44 on the fitting contacts the first ledge 31 of the entry aperture 30 which prevents further movement therethrough. However, any suitable means can be provided to align, mount and retain the working channel 26 with the entry section 10.

In the embodiment shown, the entry port section 10 is provided with a working channel aspirator 11. The aspirator generally comprises a first seal 46, a second seal 78, a housing 50 and a guide 66. In the embodiment shown, the aspirator 11 is disconnectably attached to the entry port 36 by means of the first seal 46. Alternatively, any suitable means may be provided for detachably mounting the aspirator 11 with the inspection instrument 2 such as screw threads. In addition, the present invention may be integrally formed with the inspection instrument 2. In the embodiment shown, the housing 50 has a first port 56 with an accessory tube extension 57 mounted therein and a second port 58 which communicates with the atmosphere. Alternatively, either only the first port 56 or second port 58 need be provided. Suitable means may also be provided to at least temporarily close off the first or second ports. In a preferred embodiment, both the first and second ports are provided and the extension 57 has a suitable tube attached thereto which is connected to a source of vacuum. The source of vacuum prevents gas pressure in the chamber housing 50 from reaching an elevated pressure as will be described below. In addition, the source of vacuum can aspirate the interior chamber of the housing and remove fluids and solids from therein.

The first seal 46 can generally be made of any type of suitable flexible and resilient material such as a polymer material. The seal has a general disk shape with a central slit 48 therethrough. The slit 48 of the first seal 46 is co-axially aligned with the entry aperture 30 and is generally sized and shaped to allow passage of a working instrument therethrough in addition to making a relatively tight fit therewith. Ordinarily, the seal 46 can generally seal the working channel thereby substantially preventing gases, liquids or other material which might travel up the working channel from passing through or around the first seal 46. The slit 48 is appropriately sized and the seal material appropriately resilient such that a working instrument can be passed through the first seal 46 by moving or displacing the seal material proximate the slit 48 to open a pathway for the working instrument. The material, of the first seal 46 can close around the working instrument to at least partially seal the working channel 26. However, due to the resilient nature of the seal, the movement of the working instrument into, out of and through the working channel, often incidentally carrying extraneous material past the first seal, and the less than perfect nature of the slit seal, especially when the working instrument is being removed from the inspection instrument, gases, liquids and other materials found in the body can be passed through the first seal 46. Therefore, the first seal 46, although somewhat effective, does not provide a perfect seal at all time, but merely acts as a buffer to reduce, but not necessarily eliminate, passage of materials therethrough.

Figure 2A:
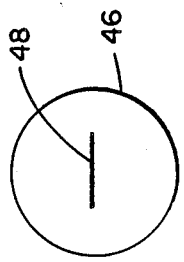
FIG. 2A is a top view of the first seal.

FIG. 2A shows a top view of the first seal 46. As shown, the seal 46 has a slit section 48 where the material of the seal has been cut. A working instrument can be inserted into and through the seal 46 wherein the material of the seal will separate to provide a channel for the passage of the working instrument. Once the working instrument is withdrawn from the seal 46 the material of the seal can close to once again close the temporary channel formed therein. Alternatively, both the first and second seals can be provided with either a cross-slit or central aperture.

The chamber housing 50 generally has a first seal chamber 59 for retaining the first seal 46 and a center aperture or chamber 60. Located at the top of the chamber housing 50 is an internally threaded section 62 and an interior ledge 64. In the embodiment shown, mounted, at least partially, in the chamber 60 is the bushing or manifold guide 66. The guide 66 has a central aperture 68 suitably sized and shaped for passage of a working instrument therethrough. The guide 66 extends down from the cap 70 towards the first seal 46 and has apertures 69 therein. The apertures 69 are provided to allow gases and extraneous material such as fluids and the like which have passed through the first seal 46 and into the guide 66 to have a path out of the central aperture 68 of the guide 66 into the chamber 60. The guide 66 also performs the function of a directional guide for guiding a working instrument during insertion into the inspection instrument 2 such that the working instrument is directed towards the central slit 48 of the first seal 46.

The cap 70 is provided at the top of the chamber housing 50. The cap 70 has a threaded section 72 which cooperatingly mates with the threaded section 62 of the housing 50. The cap 70 has a central aperture 74 for passage of the guide 66 therein and a working instrument therethrough and a seal cavity 76 for retaining the second seal or buffer 78 therein. A third seal 80, such as an O-ring, is provided to seal the cap 70 with the housing 50. The second seal 78, in this embodiment, is generally made of a resilient and flexible material such as a polymer material and is sealingly mounted in the cavity 76. Unlike the first seal 46, in this embodiment, the second seal 78 is provided with a central aperture 82 therethrough.

In operation, a physician can position the inspection instrument 2 into a patient with or without a working instrument, such as forceps, being located in the working channel 26, even if gaseous pressure has been used to widen the tract being explored. Once a target area has been identified, the physician can advance the working instrument from the working channel to preform a desired function or insert the working instrument into the inspection instrument. When the physician inserts the working instrument he inserts a leading edge of the working instrument into an inlet 84 located at the cap 70 and second seal 78. The working instrument passes through the central aperture 74 of the cap 70 and forces the material of the second seal 78 to widen at the central aperture 82. The material of the second seal 78, at least partially, closes around the intruding working instrument to at least partially form a barrier or buffer to prevent material or gases from passing therethrough.

As the working instrument is further advanced, it passes into the guide 66, through the housing 50 towards the first seal 46. As the leading edge of the working instrument advances, it passes into and through the central slit 48 of the first seal 46, at least partially extending the central slit 48 to accommodate its size and shape. The material of the first seal 46, similar to the second seal 78, at least partially, closes around the intruding working instrument to at least partially form a barrier or buffer to prevent material or gases, other than the working instrument, from passing therethrough. The working instrument can be further inserted through the entry port section 10 into the working channel 26 and, finally, to the target area at the distal end of the inspection instrument.

During the insertion, operation and removal of the working instrument, the source of vacuum can be continuously activated to remove any material that might pass through the first seal 46 into the guide 66 and chamber 60. In addition, the source of vacuum and/or the second port 58 which is open to the atmosphere can prevent pressurized gases, which might pass through the first seal 46, to build up in the chamber 60 thereby preventing these gases from exiting the inlet 84 which might otherwise occur at high velocities propelling liquids and other materials at the physician possibly imparing his vision and most certainly distracting him from his patient. As the working instrument is withdrawn, the first and second seals 46 and 78 also wipe the working instrument as it passes therethrough to at least partially clean it. In addition, the source of vacuum can at least partially remove or exit extraneous material such as liquids or other materials found in the body from the working instrument.

Figure 3:
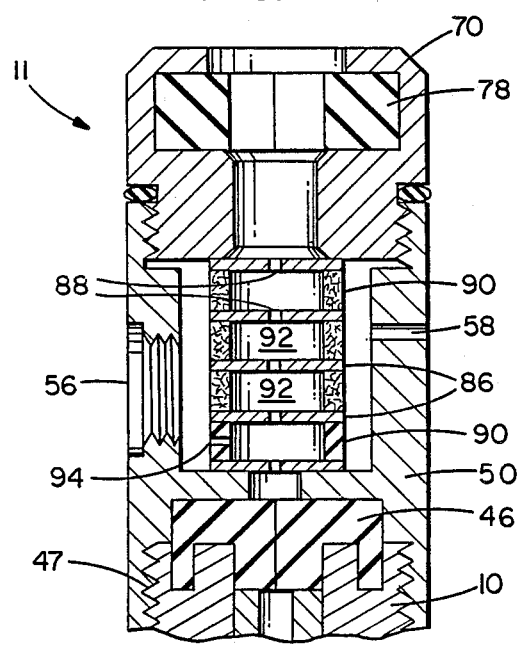
FIG. 3 is a cross-sectional view of an alternate embodiment of the invention.
Figure 3A:
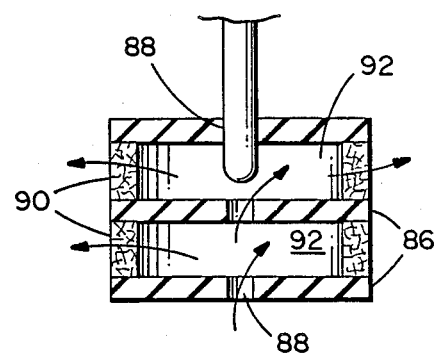
FIG. 3A is a diagrammatical cross-sectional view of seal and spacer combinations of FIG. 3.

Referring now to FIGS. 3, and 3A an alternate embodiment of the invention is shown. The housing 50, in this embodiment, comprises a cavity 47 which is shaped to cooperatingly mate with the entry port section 10 to retain the aspirator 11 on the control head 4. The first seal 46 is provided between the entry port section 10 and the aspirator 11 to seal the working channel 26. In the embodiment shown in FIG. 3, the guide 66 has been replaced by a plurality of stacked seals 86. Each of the seals 86 are similar to the first and second seals 46 and 78. Each seal 86 has a central aperture 88 therethrough and are separated by spacers 90 to form chambers 92 therebetween. The spacers 90 may either contain apertures 94 therethrough or be comprised of a woven or fiberous material similar to steel wool to allow gases to pass through.

Referring to FIG. 3A, there is shown an enlarged diagrammatical cross-sectional view of seals 86 separated by a spacers 90. The stacked seals 86, in this embodiment, preform the function of guiding the working instrument towards the working channel thus preventing the working instrument from accidentally being caught up and stopped in the chamber 60. In addition the stacked seals 86 also provide a series of wiping stations wherein the working instrument is wiped by each seal 86 as it passes therethrough to remove contaminates from the working instrument.

The spacers 90 are provided to separate the seals 86 such that multiple wipings can occur. In addition, the spacers 90 allow for chambers 92 to be formed between the seals 86. The chambers 92 each establish a plenum whereby gases or other material which pass through the first seal 46 or previous seals 86 can be collected and/or allowed to pass through or around the spacers 90 and be evacuated or otherwise removed or depressurized.

The present invention can be used with a continuous source of vacuum with the first seal 46, both with and without an instrument passing therethrough, substantially sealing the working channel 26 and thereby preventing the source of vacuum from evacuating pressurized gases used to expand the tract that the instrument 2 is traveling. In addition, the second port 58, which is open to the atmosphere, prevents the source of vacuum from creating a large vacuum in the chamber 60 which might otherwise overcome the first seal 46. Alternatively, no source of vacuum need be provided so long as any pressurized gases which pass through the first seal 46 are neutralized to prevent the otherwise pressurized gases from propelling fluid and other bodily materials from the inlet 84.

It should be understood that the foregoing description is only illustrative of the invention. Various alternatives and modifications can be devised by those skilled in the art without departing from the spirit of the invention. Accordingly, the present invention is intended to embrace all such alternatives, modifications and variances which fall within the scope of the appended claims.

What is claimed is:

1. A pressure neutralizing device for use with a working channel of an inspection instrument, the device comprising:
    frame means having a first aperture means, a second aperture means and a chamber means therebetween for passage of a working instrument therethrough, said first aperture means being positionable proximate a working channel of an inspection instrument for communication therewith;
    first pressure buffer means positioned at said first aperture means for providing a buffer between a working channel of an inspection instrument and said chamber means of the device, said first pressure buffer means being adapted to pass a working instrument therethrough;
    second pressure buffer means positioned at said second aperture means for providing a buffer between said chamber means and a working inlet of the device, said second pressure buffer means being adapted to pass a working instrument therethrough; and
    means operably coupled to said chamber means for reducing the pressure between said first and second buffer means whereby material passing through said first buffer means into said chamber means from a working channel of an inspection instrument can be substantially prevented from exiting through said working inlet at the pressure or an elevated velocity.

2. A device as in claim 1 wherein said means for reducing the pressure comprises a source of vacuum.

3. A device as in claim 1 wherein said means for reducing the pressure comprises a means for conduiting gases from said chamber means.

4. A device as in claim 3 wherein said conduit means is connected to a source of vacuum and said frame means further comprises third aperture means communicating with the atmosphere.

5. A device as in claim 1 further comprising a guide means located between said first and second buffer means for guiding a working instrument between said first and second buffer passage means.

6. A device as in claim 1 further comprising means for detachably mounting the device to an inspection instrument.

7. A device as in claim 1 wherein the device is integrally formed with an inspection instrument.

8. A device as in claim 2 further comprising means for cleaning the working instrument.

9. A device as in claim 1 wherein said means for reducing pressure comprises multiple stacked buffer means being spaced apart and forming at least two chambers, one chamber between each of said stacked buffer means, each of said stacked buffer means spaced from one another by spacer means.

10. A device as in claim 9 wherein each of said spacer means has means for passage of gases therethrough.

11. An aspirator for use with a working channel of an inspection instrument, the aspirator comprising:
    frame means forming an interior chamber means with a first aperture means and a second aperture means, said first aperture means being positionable adjacent a working channel of an inspection instrument;
    first seal means positioned at said first aperture means, said first seal means having means for passage of a working instrument therethrough;
    second seal means positioned at said second aperture means, said second seal means having means for passage of a working instrument therethrough; and
    means operably coupled to said chamber means for providing a vacuum between said first and second seal means whereby material passing through a working channel into said chamber means can be evacuated and substantially prevented from exiting through a working inlet of the aspirator.

12. An aspirator as in claim 11 wherein said first and second seal means each comprise a polymer seal.

13. An aspirator as in claim 11 wherein said first seal passage means comprises a cross-slit for passage of the working instrument therethrough.

14. An aspirator as in claim 11 wherein said passage means also wipes the working instrument when passing therethrough.

15. An aspirator as in claim 11 wherein said means for reducing pressure of gases comprises a continuous source of vacuum communicating with said chamber means.

16. An aspirator as in claim 11 further comprising a guide means located between said first and second seal means.

17. An aspirator as in claim 16 wherein said guide means forms a conduit between said passage means of said first and second seal means, said guide means having apertures therethrough for communicating said conduit with the remainder of said chamber means.

18. A method of manufacturing an aspirator for use in preventing material, such as gases, liquids and solids, form accidentally exiting a working channel of an instrument for accessing a target area of a patient, the method comprising the steps of:
    providing a frame means having a first aperture, a second aperture and a chamber therebetween, said second aperture forming a working inlet for the aspirator;
    providing a first seal means at said first aperture for positioning proximate a working channel of an instrument, first seal means being adapted to pass a working instrument therethrough;

providing a second seal means proximate said second aperture, said second seal means being adapted to pass a working instrument therethrough; and providing means for communication between the chamber and a source of vacuum for exiting at least a portion of material passed through said first seal means from a working channel of an instrument into said chamber and through an exit port whereby material passing through a working channel is substantially prevented from exiting the working inlet at the pressure or an elevated velocity.

19. A method as in claim 18 wherein the step of providing means for communication between the chamber and a source of vacuum can also further comprise the step of removing material from a working instrument in said chamber.

20. An aspirator for use with a device for accessing a target area in a patient, the device having a working channel for presenting a working instrument to a target area, the aspirator comprising:

frame means having a first aperture at a first end, a second aperture at a second end and a chamber therebetween for passage of a working instrument therethrough, one of said first or second ends forming a working inlet to said frame means;

first seal means proximate said first aperture means, said first seal means having means for passage of a working instrument therethrough;

second seal means proximate said second aperture means, said second seal means having means for passage of a working instrument therethrough; and means for providing a source of vacuum at said chamber means whereby a working instrument can be passed through said first seal means, said chamber and said second seal means and material from a working channel is substantially prevented from exiting said working inlet through the aspirator.

21. An aspirator as in claim 20 further comprising means for operably coupling the aspirator to a device for accessing a target area.

22. An aspirator as in claim 20 further comprising means for mounting the aspirator to a tube intended to be inserted into a patient.

* * * * *